United States Patent [19]

Goldbaum et al.

[11] Patent Number: 4,784,809

[45] Date of Patent: Nov. 15, 1988

[54] PROCESS FOR PREPARING PERFLUOROALKYL-ALKYL SULFONIC ACID COMPOUNDS

[75] Inventors: Richard H. Goldbaum; William R. Remington, both of Wilmington, Del.

[73] Assignee: E. I. Du Pont de Nemours and Company, Wilmington, Del.

[21] Appl. No.: 879,464

[22] Filed: Jun. 27, 1986

[51] Int. Cl.$^4$ .......................................... C07C 143/02
[52] U.S. Cl. ................................................. 260/513 R
[58] Field of Search ..................................... 260/513 R

[56] References Cited

U.S. PATENT DOCUMENTS 3,006,964 10/1961 Oesterling ............................ 260/608
3,810,939 5/1974 Ray-Chaudhurl et al. ..... 260/513 R
3,825,577 7/1974 Lalu et al. ............................ 556/111

FOREIGN PATENT DOCUMENTS 707350 4/1965 Canada ................................. 260/509

OTHER PUBLICATIONS

House Modern Synthetic Reactions 2nd Ed. (1972), pp. 292–296.

Primary Examiner—Alan Siegel
Attorney, Agent, or Firm—James E. Shipley

[57] ABSTRACT

Perfluoroalkyl-alkyl sulfonic acid compounds prepared by oxidizing the appropriate perfluoroalkyl-alkyl thiocyanate with a peroxycarboxylic acid.

50 Claims, No Drawings

PROCESS FOR PREPARING PERFLUOROALKYL-ALKYL SULFONIC ACID COMPOUNDS

BACKGROUND OF THE INVENTION

This invention relates to the preparation of perfluoroalkyl-alkyl sulfonic acid compounds and more specifically to their preparation by oxidizing the appropriate perfluoroalkyl-alkyl thiocyanate.

The perfluoroalkyl-alkyl sulfonic acid compounds of this invention are useful as surface active agents and as intermediates in the preparation of water and oil repellency agents.

U.S. Pat. No. 3,810,939 discloses a process for preparing segmented fluorocarbon sulfonic acids and related compounds by reacting a perfluoroalkyl-alkyl halide, a perfluoroalkyl olefin or a perfluoroalkyl substituted aromatic hydrocarbon with selected sulfonation reagents including alkali metal sulfites, alkali metal bisulfites, sulfuric acid, sulfur dioxide, sulfuryl chloride and chlorosulfonic acid. Derivatives of the fluorocarbon sulfonic acids including acid anhydrides, metal salts, sulfonyl halides, and sulfonamides are disclosed.

U.S. Pat. No. 3,825,577 discloses a method of preparing perfluoroalkyl-alkyl sulfonic acid compounds by oxidizing a perfluoroalkyl-alkyl thiocyanate with chlorine or bromine to form a perfluoroalkyl-alkyl sulfonyl halide; thereafter, this compound is neutralized with a base to form compounds having the following formula:

$$C_nF_{2n+1}(CH_2)_bSO_3M,$$

wherein
n=1 to 20,
b=2 to 20, and
M=a metal of Groups IA, IIA, IB, IIB, VIII, NH$_4$, aluminum or lead radical.

This patent discloses that the perfluoroalkyl-alkyl sulfonic acid compounds can also be formed by reacting a perfluoroalkyl-alkyl halide with a metal sulfite to form compounds having the same formula shown above.

SUMMARY OF THE INVENTION

The process of this invention comprises oxidizing a perfluoroalkyl-alkyl thiocyanate of the following formula:

$$C_nF_{2n+1}(CH_2)_bSCN,$$

wherein
n=1 to 20, and
b=2 to 20 with a peroxycarboxylic acid having the following formula:

$$R(CO_3H)_n,$$

wherein
R=an alkyl, aralkyl, cycloalkyl, aryl, or heterocyclic group, and
n=1 or 2, at effective process conditions to produce a reaction mass containing perfluoroalkyl-alkyl sulfonic acid compounds having the following formula:

$$C_nF_{2n+1}(CH_2)_bSO_3M,$$

wherein
n=1 to 20,
b=2 to 20, and
M=H or NH$_4$.

Thereafter, the reaction mass can be held at a sufficient temperature for a sufficient time period and/or a catalyst can be added to cause unreacted peroxygen compounds to decompose.

Also included within the scope of this invention is a technique for concentrating the desired perfluoroalkyl-alkyl sulfonic acid compounds by distillation.

DETAILED DESCRIPTION OF THE INVENTION

Perfluoroalkyl-alkyl thiocyanates are the intermediates for the process of this invention and can be oxidized with a peroxycarboxylic acid, preferably peracetic, performic, peroxypropionic, peroxybutyric or m-chloroperbenzoic acid, and more preferably peracetic acid, at effective process conditions to obtain perfluoroalkyl-alkyl sulfonic acid compounds according to the following equations (using peracetic acid as the representative peroxycarboxylic acid):

$$C_nF_{2n+1}(CH_2)_bSCN + 3CH_3COOOH + 2H_2O \rightarrow C_nF_{2n+1}(CH_2)_bSO_3NH_4 + CO_2 + 3CH_3COOH \quad (a)$$

$$C_nF_{2n+1}(CH_2)_bSCN + 2CH_3COOOH + H_2O \rightarrow C_nF_{2n+1}(CH_2)_bSO_3H + HCN + 2CH_3COOH \quad (b)$$

wherein n=1 to 20 and b=2 to 20. Mixtures of discrete sulfonic acid compounds are formed.

By effective process conditions is meant process conditions as exemplified below which can be used to oxidize a perfluoroalkyl-alkyl thiocyanate with a peroxycarboxylic acid to obtain the indicated perfluoroalkyl-alkyl sulfonic acid compounds and mixtures thereof.

Great Britain Pat. No. 1,218,760 discloses a method for preparing perfluoroalkyl-alkyl thiocyanates by reacting a chloride, bromide or iodide having the following formula:

$$C_nF_{2n+1}(CH_2)_bY,$$

wherein
n=1 to 20,
b=2 to 20, and
Y=Cl, Br or I, with a thiocyanate having the formula M(SCN)$_b$, where M represents hydrogen, the ammonium radical or a metal from Groups IA, IB, IIA, IIB, VIII, or an aluminum or lead radical and b is a number equal to the valency of M, to form a perfluoroalkyl-alkyl thiocyanate having the following formula:

$$C_nF_{2n+1}(CH_2)_bSCN,$$

wherein
n=1 to 20, and
b=2 to 20.

A preferred embodiment of preparing the intermediate is to react perfluoroalkyl-alkyl iodide with sodium thiocyanate in isopropyl alcohol to produce a crude perfluoroalkyl-alkyl thiocyanate and sodium iodide according to the following equation:

$$C_nF_{2n+1}(CH_2)_bI + NaSCN \rightarrow C_nF_{2n+1}(CH_2)_bSCN + NaI$$

wherein:

n=4 and even numbers to 20 with an average of 8
b=2.

Thereafter, the major portion of the isopropyl alcohol can be removed by distillation, and salts can be removed with water washes. This reaction and isolation procedure can be repeated to ensure more complete conversion.

The oxidation reaction of the instant invention can be carried out in a reactor which is equipped with facilities for feeding, agitating, heating, and cooling the reactants, and can withstand the corrosivity of the raw materials and reactants. It has been found that a reactor lined with glass or "Teflon" perfluorocarbon resin is particularly effective in withstanding this corrosivity. It is important that proper materials of construction be used since corrosion products can lead to the decomposition of the peroxycarboxylic acids.

To facilitate easier handling of the intermediate and to enhance initiation of the process, the intermediate can be heated prior to its introduction into the reactor. Generally, a temperature of about 65 to 105 degrees Celsius is preferred while a temperature of about 85 to 100 degrees Celsius is more preferred to accomplish this.

The peroxycarboxylic acid can be used at any concentration which can be handled safely. For example, a 20 to 50 percent concentration of peracetic acid in a solution of acetic acid, water and hydrogen peroxide would be usable with the preferred concentration of peracetic acid in the 30 to 40 percent range. A 35 percent concentration grade of peracetic acid containing about 10.7 percent active oxygen (7.5% active oxygen as peracetic acid and 3.2% active oxygen as hydrogen peroxide) is commercially available and is most preferred.

A ratio of moles of total active oxygen contained in the peroxycarboxylic acid per mole of intermediate of about 2 to 5 is preferred while a ratio of 2.5 to 4 is more preferred. In the case of the peracetic acid solution described above, which contains both peracetic acid and hydrogen peroxide, the total active oxygen is the sum of the contributions from both the peracetic acid and the hydrogen peroxide.

The reaction which occurs when the peroxycarboxylic acid is added to the thiocyanate intermediate is exothermic and cooling must be provided to the reaction mass. The peroxycarboxylic acid can be added to the thiocyanate intermediate at any rate which is possible as determined by the cooling capability of the reactor. However, an addition time of about 1 to 20 hours is preferred, about 3 to 16 hours is more preferred, and about 3 to 8 hours is most preferred. It is desirable to maintain a temperature during the addition of the peroxycarboxylic acid of between about 65 and 105 degrees Celsius while a temperature between about 85 and 100 degrees Celsius is preferred. Agitation of the thiocyanate intermediate should be provided during the addition of the peroxycarboxylic acid.

The time required for the oxidation reaction to be completed varies with the temperature and pressure which are applied to the reactants; it is desirable to hold and continue agitating the reaction mass in the reactor after the peroxycarboxylic acid addition is completed to allow for further reaction to occur. It has been found that this reaction may be essentially completed if the reaction mass is held and agitated for about an additional 1 to 20 hours after the peroxycarboxylic acid addition is completed while maintaining a temperature of about 65 to 105 degrees Celsius. The preferred conditions for completing this oxidation reaction during this hold period are a temperature of about 90 to 100 degrees Celsius and a time of about 3 to 16 hours.

The oxidation reaction of the instant invention can also be accomplished by generating the peroxycarboxylic acid in the reactor. For example, in the case of peracetic acid, this can be done by combining the thiocyanate intermediate and acetic acid in the reactor first and thereafter adding hydrogen peroxide with agitation. Sufficient sulfuric acid to act as a catalyst for converting acetic acid to peracetic acid can also be added with the acetic acid. In another example, acetic anhydride can be combined with the thiocyanate intermediate and thereafter hydrogen peroxide can be added. An excess of acetic anhydride at the end of the oxidation reaction should be avoided due to the potential formation of explosive diacetyl peroxide. Peracetic acid will be generated in both examples which will thereafter oxidize the thiocyanate intermediate as previously described. Performic acid can be generated in a similar manner.

The oxidation reaction of this invention can be run at subatmospheric, atmospheric or superatmospheric pressure.

After the oxidation reaction is essentially complete, the reaction mass may be held for an additional period at a selected temperature to decompose unreacted peroxygen compounds. Agitation of the reaction mass during this decomposition is desirable. The preferred temperature for this decomposition is 80 to 105 degrees Celsius while the more preferred temperature is 90 to 100 degrees Celsius. The preferred hold period for this decomposition is 10 to 25 hours.

It has also been found that the addition of a salt containing a metal from Groups IB, IIB, VIB, VIIB, or VIII, preferably a metal such as iron, chromium, copper, cobalt, or nickel, accelerates the decomposition of residual peroxygen compounds. The amount of the metal in the salt which is preferred to accomplish this accelerated decomposition can be between about 0.001 and 0.1 percent of the weight of the initial charge of the thiocyanate intermediate. The more preferred amount of the metal contained in the salt is between about 0.005 and 0.015 percent on the same basis. The length of time required to decompose the peroxygen compounds will vary but it has been found that the peroxygen compounds can be reduced to less than about 0.1 percent based on the weight of the reaction mass if the reaction mass is held for 1 to 20 hours at a temperature of about 80 to 105 degrees Celsius while preferred conditions are a hold time of 5 to 16 hours and a temperature of about 90 to 100 degrees Celsius.

After peroxygen compounds are decomposed to a desired level, distillation can be used to concentrate the reaction mass by removing volatile components. Methods used to distill are well known and a wide range of temperatures and pressures can be used. For example, when peracetic acid is used as the oxidizer, a final temperature of about 120 to 150 degrees Celsius and atmospheric pressure are preferred to reduce the quantity of the volatile components of acetic acid and water in the reaction mass. This distillation can be continued until the desired concentration of the compounds of this invention is obtained.

Thereafter, the concentration of the compounds of this invention can be adjusted to a desired level by adding the distilled reaction mass to a known amount of water.

The principal hazards of the oxidation reaction relate to the use of the peroxycarboxylic acids and the generation of hydrogen cyanide in the reactor during the reaction. Hydrogen cyanide evolved from the reaction can be converted to sodium cyanide in a caustic scrubber. In addition, the oxygen generated from the decomposition of active oxygen compounds can be kept at low levels with a nitrogen sweep to avoid flammable mixtures.

The following examples further illustrate this invention.

EXAMPLE 1

A one liter three-neck round-bottom glass flask was equipped with the following: agitator, water-cooled reflux condenser, thermometer, nitrogen inlet, and a dropping funnel for peracetic acid. The exit of the condenser was connected to a scrubber containing 400 g of 15% sodium hydroxide to trap the hydrogen cyanide which was evolved. A mixture of thiocyanates with the formula $C_nF_{2n+1}(CH_2)_2SCN$ (350 g), where n=4, 6, 8, 10, 12, 14, 16, 18, and 20 with n=8 on average with approximate weight distribution as follows:

| n | wt % |
|---|---|
| 4 | 4 max. |
| 6 | 30–42 |
| 8 | 28–33 |
| 10 | 15–17 |
| 12 | |
| 14 | |
| 16 | 15.5 max. |
| 18 | | and with an average molecular weight of 505 was weighed into the flask. The nitrogen flow was adjusted to approximately 375 cc/min and held at this rate for the entire oxidation. The contents of the flask were heated to 75 degrees Celsius by applying heat to the flask with a heating mantle. Commercial 35% peracetic acid (375 g) was placed in the dropping funnel. (This amount of commercial peracetic acid represented 3.6 moles of active oxygen compounds per mole of thiocyanate intermediate.) The peracetic acid was added dropwise to the thiocyanate with agitation over a period of 3.8 hours while maintaining a reaction temperature of 65 to 70 degrees Celsius by cooling with an ice bath. The reaction mass was then held with agitation at 65 plus or minus 2 degrees Celsius for 19 hours. The resulting reaction mass contained 268 g of the sulfonic acid compounds of this invention which represented a yield of 72.1%.

The amount of the sulfonic acid compounds contained in the reaction mass was determined as follows. A 10 ml aliquot of a fluoropolymer dispersion dispersed in water with an anionic surfactant was added to each of two beakers. Deionized water (100 ml) was then added to each beaker. A sample of the reaction mass (0.04 to 0.08 g) was added to one beaker. The contents of each beaker were agitated and titrated with an aqueous solution of cetyl trimethyl ammonium bromide (CTMAB) of known concentration. The endpoint of the titration was determined when the dispersion was completely coagulated, i.e., when a clear supernatant was obtained after the stirring was stopped. The amount of sulfonic acid compounds as a percent of the total reaction mass was determined from the following equation:

$$\% \text{ Sulfonic acid compounds} = \frac{(A - B)(0.1)(C)(D)}{W}$$

where:
A = Volume of CTMAB for sample, ml
B = Volume of CTMAB for blank, ml
C = Concentration of CTMAB, moles/l
D = Equivalent wt of the sulfonic acid compounds
W = Wt of sample, g

EXAMPLE 2

A one liter three-neck round-bottom glass flask was equipped as described in Example 1. The exit of the condenser was connected to a scrubber containing 400 grams of 15% sodium hydroxide to trap the hydrogen cyanide evolved. $C_nF_{2n+1}(CH_2)_2SCN$ (300 g) as described in Example 1 was weighed into the flask. The nitrogen flow was adjusted to approximately 200 cc/min and held at this rate for the entire oxidation through the atmospheric distillation. The contents of the flask was heated to 98 degrees Celsius by applying heat to the flask with a heating mantle. Commercial 35% peracetic acid (326 g) was placed in the dropping funnel. The peracetic acid was added dropwise to the thiocyanate with agitation over a period of 5.6 hours while maintaining a reaction temperature of 90 to 100 degrees Celsius by cooling with an ice bath. The reaction mass was then held with agitation at 95 plus or minus 3 degrees Celsius for 3.1 hours at which time of $CuSO_4 \cdot 5H_2O$ (0.12 g) was added to aid decomposition of the residual peroxygen compounds. The reaction mass was thereafter held with agitation at 95 plus or minus 3 degrees Celsius for 15 hours. The condenser was then rearranged for downward distillation of acetic acid and water from the reaction mass. During this distillation, the reaction mass was gradually heated to 140 degrees Celsius at atmospheric pressure. Thereafter, the reaction mass was cooled to about 120 degrees Celsius. Then the pressure was slowly reduced to less than 2 mm Hg and at the same time the temperature was slowly increased to 130 degrees Celsius. The resulting solids weighed 308 g and contained 295 g of the sulfonic acid compounds of this invention as calculated by the method described in Example 1. This represented a yield of 92.5%.

EXAMPLE 3

A one liter three-neck round-bottom glass flask was equipped as described in Example 1. The exit of the condenser was connected to a scrubber containing 400 g of 15% sodium hydroxide to trap the hydrogen cyanide which was evolved. $C_nF_{2n+1}(CH_2)_2SCN$ (300 g) as described in Example 1 was weighed into the flask. The nitrogen flow was adjusted to approximately 47 cc/min and held at this rate for the entire oxidation through the distillation. The contents of the flask were heated to 95 degrees Celsius by applying heat to the flask with a heating mantle. Commercial 31.6% peracetic acid (445 g) was placed in the dropping funnel. The peracetic acid was added dropwise to the thiocyanate with agitation over a period of 1.4 hours while maintaining a reaction temperature of 90 to 100 degrees Celsius by cooling with an ice bath. The reaction mass was then held with agitation at 95 plus or minus 2 degrees Celsius for 3 hours at which time $CuSO_4 \cdot 5H_2O$ (0.12 g) was added. The reaction mass was then held with agitation at 95 plus or minus 3 degrees Celsius for 17.5 hours. The condenser was rearranged for downward distillation of acetic acid and water from the reaction mass. The reaction mass was gradually heated to 141 degrees Celsius at atmospheric pressure. The residue in the flask contained 252 g of sulfonic acid compounds as determined by the method described in Example 1. This represented a yield of 79.0%.

EXAMPLE 4

A 10 gallon glass-lined steel kettle was equipped with the following: glass-coated agitator, glass-lined water-cooled reflux condenser, "Teflon" perfluorocarbon resin-sheathed thermocouple, and a nitrogen inlet. The exit of the condenser was connected to a caustic scrubber (packed column with counter-current flow of caustic). $C_nF_{2n+1}(CH_2)_2SCN$ (36.8 pounds) as described in Example 1 was liquified by heating in an oven at 80 degrees Celsius. This material was added to the glass-lined reactor and heated to a temperature of 95 degrees Celsius. Commercial 35% peracetic acid (40 pounds) was metered into the reactor using a diaphram pump constructed so that the only materials which contacted the peracetic acid were 316 stainless steel and "Teflon" perfluorocarbon resin. The peracetic acid was added with agitation over a period of 5.3 hours while maintaining a temperature of 90 to 100 degrees Celsius. The nitrogen flow rate was adjusted to maintain the percent oxygen at less than or equal to 8% at the scrubber exit throughout the oxidation, distillation and dilution. The reaction mass was then held with agitation at 95 plus or minus 5 degrees Celsius for 6 hours at which time CuSO$_4$.5H$_2$O (6.6 g) was added and the reaction mass was then held with agitation at 95 plus or minus 5 degrees Celsius for an additional 12 hours. Thereafter, the condenser was rearranged for downward distillation and the reaction mass was gradually heated at atmospheric pressure until 140 degrees Celsius was reached. Thereafter, the resulting mass was cooled to 120 degrees Celsius and diluted to 38.5% sulfonic acid compounds (as determined by the method described in Example 1) by the addition of 50 pounds of deionized water. Total weight of the diluted product of this invention was 94.7 pounds. This represented a yield of 93%.

EXAMPLE 5

A one liter three-neck round-bottom glass flask was equipped as described in Example 1. The exit of the condenser was connected to a scrubber containing 400 g of 15% sodium hydroxide to trap the hydrogen cyanide evolved. $C_nF_{(2n+1)}(CH_2)_2SCN$ (300 g) as described in Example 1 was weighed into the flask. The nitrogen flow was adjusted to approximately 47 cc/min and held at this rate for the entire oxidation through distillation. The thiocyanate was heated to 94 degrees Celsius by applying heat to the flask with a heating mantle. Commercial 31.6% peracetic acid (445 g) was placed in the dropping funnel. The peracetic acid was added dropwise to the thiocyanate with agitation over a period of 1.2 hours while maintaining a reaction temperature of 80 to 100 degrees Celsius by cooling with an ice bath. The reaction mass was then held with agitation at 85 degrees Celsius for 1.5 hours. A sample of the reaction mass was removed from the reactor and was determined by analysis to contain 7.8% peracetic acid and 1.2% hydrogen peroxide. The reaction mass temperature was increased to 95 degrees Celsius and then held with agitation for one additional hour at which time another sample was taken and determined by analysis to contain 6.1% peracetic acid and 0.97% hydrogen peroxide. Thereafter, FeSO$_4$.7H$_2$O (equivalent to 27 ppm iron based on the wt. of the initial charge of thiocyanate intermediate), NiSO$_4$.6H$_2$O (equivalent to 20 ppm nickel on same basis), and CrCl$_3$.6H$_2$O (equivalent to 50 ppm chromium on same basis), were added. The reaction mass was maintained at 95 to 98 degrees Celsius with agitation for 1.3 hours. A sample of the reaction mass was determined by analysis to contain 0.9% peracetic acid and 0.3% hydrogen peroxide. After an additional 16 hours with agitation at 95 degrees Celsius, the reaction mass was again analyzed and determined to contain 0.01% peracetic acid and 0.01% hydrogen peroxide. The condenser was rearranged for downward distillation and the reaction mass was gradually heated with agitation at atmospheric pressure until a temperature of 141 degrees Celsius was reached. The resulting reaction mass contained 227 g of the sulfonic acid compounds of this invention as determined by the method described in Example 1. This represented a yield of 71.3%.

EXAMPLE 6

A one liter three-neck round-bottom glass flask was equipped as described in Example 1. The exit of the condenser was connected to a scrubber containing 400 g of 15% sodium hydroxide to trap the hydrogen cyanide evolved during the reaction. The thiocyanate as described in Example 1 (300 g) was weighed into the flask. Nitrogen flow through the reactor was adjusted to approximately 375 cc/min and held at this rate for the entire oxidation. The contents of the flask were heated to 100 degrees Celsius by applying heat to the reactor with a heating mantle. Commercial 29.9% peracetic acid (350 g) was placed in the dropping funnel. The peracetic acid was added dropwise to the thiocyanate with agitation over a period of 2.5 hours while maintaining a reaction temperature of 100 to 105 degrees Celsius by cooling with an ice bath. The reaction mass was thereafter held with agitation for 18 hours at 100 degrees Celsius. The resulting mass contained 253 g of the sulfonic acid compounds of this invention as determined by the method described in Example 1. This represented a yield of 79.5%.

We claim:

1. A process for the manufacture of perfluoroalkylalkyl sulfonic acid compounds, having the formula:

$$C_nF_{2n+1}(CH_2)_bSO_3M$$

wherein
n=1 to 20,
b=2 to 20, and
M=H or NH$_4$,
comprising oxidizing the corresponding perfluoroalkylalkyl thiocyanate having the formula:

$$C_nF_{2n+1}(CH_2)_bSCN$$

wherein
n=1 to 20, and
b=2 to 20,
with a peroxycarboxylic acid having the following formula:

$$R(CO_3H)_n$$

wherein

R=an alkyl, aralkyl, cycloalkyl, aryl, or heterocyclic group, and
n=1 or 2,
at effective process conditions to form a reaction mass containing the perfluoroalkyl-alkyl sulfonic acid compounds, wherein cooling is provided during the oxidizing step.

2. The process of claim 1 wherein the amount of peroxycarboxylic acid used in the oxidation reaction is about 2 to 5 moles of peroxycarboxylic acid per mole of thiocyanate.

3. The process of claim 2 wherein the amount of peroxycarboxylic acid used in the oxidation reaction is about 2.5 to 4 moles of peroxycarboxylic acid per mole of thiocyanate.

4. The process of claim 1 wherein the peroxycarboxylic acid is selected from the group consisting of peracetic, performic, peroxypropionic, peroxybutyric, and m-chloroperbenzoic acid.

5. The process of claim 2 wherein the peroxycarboxylic acid is selected from the group consisting of peracetic, performic, peroxypropionic, peroxybutyric, and m-chloroperbenzoic acid.

6. The process of claim 3 wherein the peroxycarboxylic acid is selected from the group consisting of peracetic, performic, peroxypropionic, peroxybutyric, and m-chloroperbenzoic acid.

7. The process of claim 1 wherein the peroxycarboxylic acid is peracetic acid.

8. The process of claim 2 wherein the peroxycarboxylic acid is peracetic acid.

9. The process of claim 3 wherein the peroxycarboxylic acid is peracetic acid.

10. The process of claim 7 wherein the peracetic acid is added to the thiocyanate as a solution with acetic acid, water and hydrogen peroxide.

11. The process of claim 8 wherein the peracetic acid is added to the thiocyanate as a solution with acetic acid, water and hydrogen peroxide.

12. The process of claim 9 wherein the peracetic acid is added to the thiocyanate as a solution with acetic acid, water and hydrogen peroxide.

13. The process of claim 1 wherein the oxidation reaction occurs at a temperature of about 65 to 105 degrees Celsius and the peroxycarboxylic acid is added to the thiocyanate with agitation over a period of about 1 to 20 hours.

14. The process of claim 2 wherein the oxidation reaction occurs at a temperature of about 65 to 105 degrees Celsius and the peroxycarboxylic acid is added to the thiocyanate with agitation over a period of about 1 to 20 hours.

15. The process of claim 3 wherein the oxidation reaction occurs at a temperature of about 65 to 105 degrees Celsius and the peroxycarboxylic acid is added to the thiocyanate with agitation over a period of about 1 to 20 hours.

16. The process of claim 4 wherein the oxidation reaction occurs at a temperature of about 65 to 105 degrees Celsius and the peroxycarboxylic acid is added to the thiocyanate with agitation over a period of about 1 to 20 hours.

17. The process of claim 5 wherein the oxidation reaction occurs at a temperature of about 65 to 105 degrees Celsius and the peroxycarboxylic acid is added to the thiocyanate with agitation over a period of about 1 to 20 hours.

18. The process of claim 6 wherein the oxidation reaction occurs at a temperature of about 65 to 105 degrees Celsius and the peroxycarboxylic acid is added to the thiocyanate with agitation over a period of about 1 to 20 hours.

19. The process of claim 1 wherein the oxidation reaction occurs at a temperature of about 85 to 100 degrees Celsius and the peroxycarboxylic acid is added to the thiocyanate with agitation over a period of about 3 to 8 hours.

20. The process of claim 2 wherein the oxidation reaction occurs at a temperature of about 85 to 100 degrees Celsius and the peroxycarboxylic acid is added to the thiocyanate with agitation over a period of about 3 to 8 hours.

21. The process of claim 3 wherein the oxidation reaction occurs at a temperature of about 85 to 100 degrees Celsius and the peroxycarboxylic acid is added to the thiocyanate with agitation over a period of about 3 to 8 hours.

22. The process of claim 4 wherein the oxidation reaction occurs at a temperature of about 85 to 100 degrees Celsius and the peroxycarboxylic acid is added to the thiocyanate with agitation over a period of about 3 to 8 hours.

23. The process of claim 5 wherein the oxidation reaction occurs at a temperature of about 85 to 100 degrees Celsius and the peroxycarboxylic acid is added to the thiocyanate with agitation over a period of about 3 to 8 hours.

24. The process of claim 6 wherein the oxidation reaction occurs at a temperature of about 85 to 100 degrees Celsius and the peroxycarboxylic acid is added to the thiocyanate with agitation over a period of about 3 to 8 hours.

25. The process of claim 1 further comprising the step of holding the reaction mass at a temperature of about 65 to 105 degrees Celsius for about 1 to 20 hours with agitation after the peroxycarboxylic acid and the thiocyanate have been combined to allow for more complete oxidation to occur.

26. The process of claim 25 wherein the holding step includes holding the reaction mass at about 90 to 100 degrees Celsius for about 3 to 16 hours after the peroxycarboxylic acid and the thiocyanate have been combined to allow for more complete oxidation to occur.

27. The process of claim 1 further comprising the step of decomposing any unreacted peroxygen compound.

28. The process of claim 25 further comprising the step of decomposing any unreacted peroxygen compound.

29. The process of claim 26 further comprising the step of decomposing any unreacted peroxygen compound.

30. The process of claim 27 wherein the decomposing step is accelerated by adding to the reaction mass a metal salt and, thereafter, holding the reaction mass at a temperature of about 80 to 105 degrees Celsius for a period of about 1 to 20 hours and wherein the metal in the metal salt is selected from the groups of metals consisting of Groups IB, IIB, VIB, VIIB, and VIII.

31. The process of claim 28 wherein the decomposing step is accelerated by adding to the reaction mass a metal salt and, thereafter, holding the reaction mass at a temperature of about 80 to 105 degrees Celsius for a period of about 1 to 20 hours and wherein the metal in the metal salt is selected from the groups of metals consisting of Groups IB, IIB, VIB, VIIB, and VIII.

32. The process of claim 29 wherein the decomposing step is accelerated by adding to the reaction mass a metal salt and, thereafter, holding the reaction mass at a temperature of about 80 to 105 degrees Celsius for a period of about 1 to 20 hours and wherein the metal in the metal salt is selected from the groups of metals consisting of Groups IB, IIB, VIB, VIIB, and VIII.

33. The process of claim 30 wherein the metal in the metal salt is selected from the group consisting of iron, chromium, copper, cobalt and nickel.

34. The process of claim 31 wherein the metal in the metal salt is selected from the group consisting of iron, chromium, copper, cobalt and nickel.

35. The process of claim 32 wherein the metal in the metal salt is selected from the group consisting of iron, chromium, copper, cobalt and nickel.

36. The process of claim 25 further comprising the step of distilling volatile components from the reaction mass to concentrate the perfluoroalkyl-alkyl sulfonic acid compounds.

37. The process of claim 26 further comprising the step of distilling volatile components from the reaction mass to concentrate the perfluoroalkyl-alkyl sulfonic acid compounds.

38. The process of claim 27 further comprising the step of distilling volatile components from the reaction mass to concentrate the perfluoroalkyl-alkyl sulfonic acid compounds.

39. The process of claim 28 further comprising the step of distilling volatile components from the reaction mass to concentrate the perfluoroalkyl-alkyl sulfonic acid compounds.

40. The process of claim 29 further comprising the step of distilling volatile components from the reaction mass to concentrate the perfluoroalkyl-alkyl sulfonic acid compounds.

41. The process of claim 30 further comprising the step of distilling volatile components from the reaction mass to concentrate the perfluoroalkyl-alkyl sulfonic acid compounds.

42. The process of claim 31 further comprising the step of distilling volatile components from the reaction mass to concentrate the perfluoroalkyl-alkyl sulfonic acid compounds.

43. The process of claim 32 further comprising the step of distilling volatile components from the reaction mass to concentrate the perfluoroalkyl-alkyl sulfonic acid compounds.

44. The process of claim 33 further comprising the step of distilling volatile components from the reaction mass to concentrate the perfluoroalkyl-alkyl sulfonic acid compounds.

45. The process of claim 34 further comprising the step of distilling volatile components from the reaction mass to concentrate the perfluoroalkyl-alkyl sulfonic acid compounds.

46. The process of claim 35 further comprising the step of distilling volatile components from the reaction mass to concentrate the perfluoroalkyl-alkyl sulfonic acid compounds.

47. The process of claim 1 wherein the peroxycarboxylic acid is peracetic acid which is formed by combining acetic acid and the perfluoroalkyl-alkyl thiocyanate and thereafter adding hydrogen peroxide with agitation over a period of about 1 to 20 hours to combine with the acetic acid to form peracetic acid.

48. The process of claim 47 wherein sufficient sulfuric acid to act as a catalyst for converting acetic acid to peracetic acid is added with the acetic acid.

49. The process of claim 1 wherein the peroxycarboxylic acid is performic acid which is formed by combining formic acid and the perfluoroalkyl-alkyl thiocyanate and thereafter adding hydrogen peroxide with agitation over a period of about 1 to 20 hours to combine with the formic acid to form performic acid.

50. The process of claim 25 wherein the hydrogen cyanide which is formed during the oxidizing and holding steps is converted to sodium cyanide by contacting the hydrogen cyanide with sodium hydroxide in a scrubbing operation.

* * * * *